United States Patent [19]

Moran

[11] 4,078,895

[45] Mar. 14, 1978

[54] SAMPLE DISPENSING SYSTEM IN AN AUTOMATIC CHEMICAL TESTING APPARATUS

[75] Inventor: John J. Moran, Houston, Tex.

[73] Assignee: Hycel, Inc., Houston, Tex.

[21] Appl. No.: 725,270

[22] Filed: Sep. 21, 1976

[30] Foreign Application Priority Data

Mar. 17, 1976 United Kingdom ............... 10685/76

[51] Int. Cl.² ........................ G01N 1/10; G01N 33/16
[52] U.S. Cl. .................................. 23/253 R; 23/259; 141/130
[58] Field of Search ................. 23/230 R, 253 R, 259; 141/130

[56] References Cited

U.S. PATENT DOCUMENTS

| 3,644,095 | 2/1972 | Netheler et al. | 23/259 |
| 3,728,079 | 4/1973 | Moran | 23/259 X |
| 3,854,879 | 12/1974 | Figueroa | 23/230 R |
| 3,883,305 | 5/1975 | Hoskins et al. | 23/253 R |
| 3,985,508 | 10/1976 | Williams | 23/253 R |

*Primary Examiner*—R.E. Serwin
*Attorney, Agent, or Firm*—Robert P. Cogan

[57] ABSTRACT

In an automatic chemical testing apparatus, means are provided for dispensing aliquots of a sample to reaction containers. A carriage means housing a self-priming hydraulic circuit mounted for motion on a support arm housing drive means. During an operating cycle, control means operate the drive means to position a conduit communicating with the hydraulic circuit over a sample source and aspirate an amount of the serum into the hydraulic circuit. The carriage means is then moved, preferably at uniform rate over a row and dispensing means are pulsed to dispense samples into individual reaction containers while the carriage means is moving. The carriage means is then returned to its starting position.

22 Claims, 6 Drawing Figures

SAMPLE DISPENSING SYSTEM IN AN AUTOMATIC CHEMICAL TESTING APPARATUS

BACKGROUND OF THE INVENTION

This invention relates to automatic chemical testing apparatus and more particularly to means for providing sample aliquots to reaction containers.

The present invention contemplates improvement in the type of automatic chemical testing apparatus disclosed in U.S. Pat. No. 3,728,079 issued Apr. 17, 1973 to John J. Moran and assigned to the assignee herein, the disclosure of which is incorporated herein by reference. More particularly, the present invention contemplates an improvement in the type of sample fluid dispensing means in such automatic chemical testing apparatus disclosed in U.S. Pat. No. 3,716,338 issued Feb. 19, 1973 to John J. Moran also commonly assigned and incorporated herein by reference. In chemical testing apparatus of the type contemplated herein, a sample, for example human serum, is provided at a sample source, and aliquots of the sample are dispensed into individual reaction containers, each reaction container being utilized for determination of the concentration of a different substance in the sample. The reaction containers are indexed through successive positions for incubation and addition of reagents thereto, and the reacted contents of each reaction container are withdrawn for analysis by readout means such as spectrophotometric analysis means and associated signal translation and printout for display circuitry.

Necessary attributes of a successful system include ability to deliver aliquots from successive samples without intersample contamination, ease of fluid handling and in improved forms, speed of the dispensing operation. It is desirable to reduce the length of conduits through which samples run past compared to, for example, the type of apparatus disclosed in U.S. Pat. No. 3,799,744 to Jones. Further, it is important to select a reduced amount of sample to be withdrawn from a sample source if desired, since the amount of sample available is generally limited.

SUMMARY OF THE INVENTION

It is therefore an object of the present invention to provide sample dispensing means for an automatic chemical testing apparatus capable of withdrawing samples from a source, dispensing aliquots of the sample to individual reaction containers and achieving this with increased speed compared to prior analyzers.

It is a further object of the present invention to provide an apparatus of the type described which is reliable in operation and has a simplified mechanical drive.

It is also an object of the present invention to provide an apparatus of the type described in which interfacing with electronic control circuitry is facilitated.

Briefly stated, in accordance with the present invention, serum dispensing and aspirating means are provided in a carriage mounted on an arm containing drive means coupled thereto. The carriage includes a self-priming hydraulic circuit including aspiration and dispensing pumps operated by control circuity synchronized with drive circuitry. Dispensing may be performed while the carriage is moving.

BRIEF DESCRIPTION OF THE DRAWINGS

The means by which the foregoing objects and features of the invention are pointed out with particularity in the claims forming the concluding portion of the specification. The invention, both as to its organization and manner of operation may be further understodd by reference to the following description taken in connection with the following drawings.

Of the drawings.

DESCRIPTION OF THE PREFERRED EMBODIMENT

Figure 1:
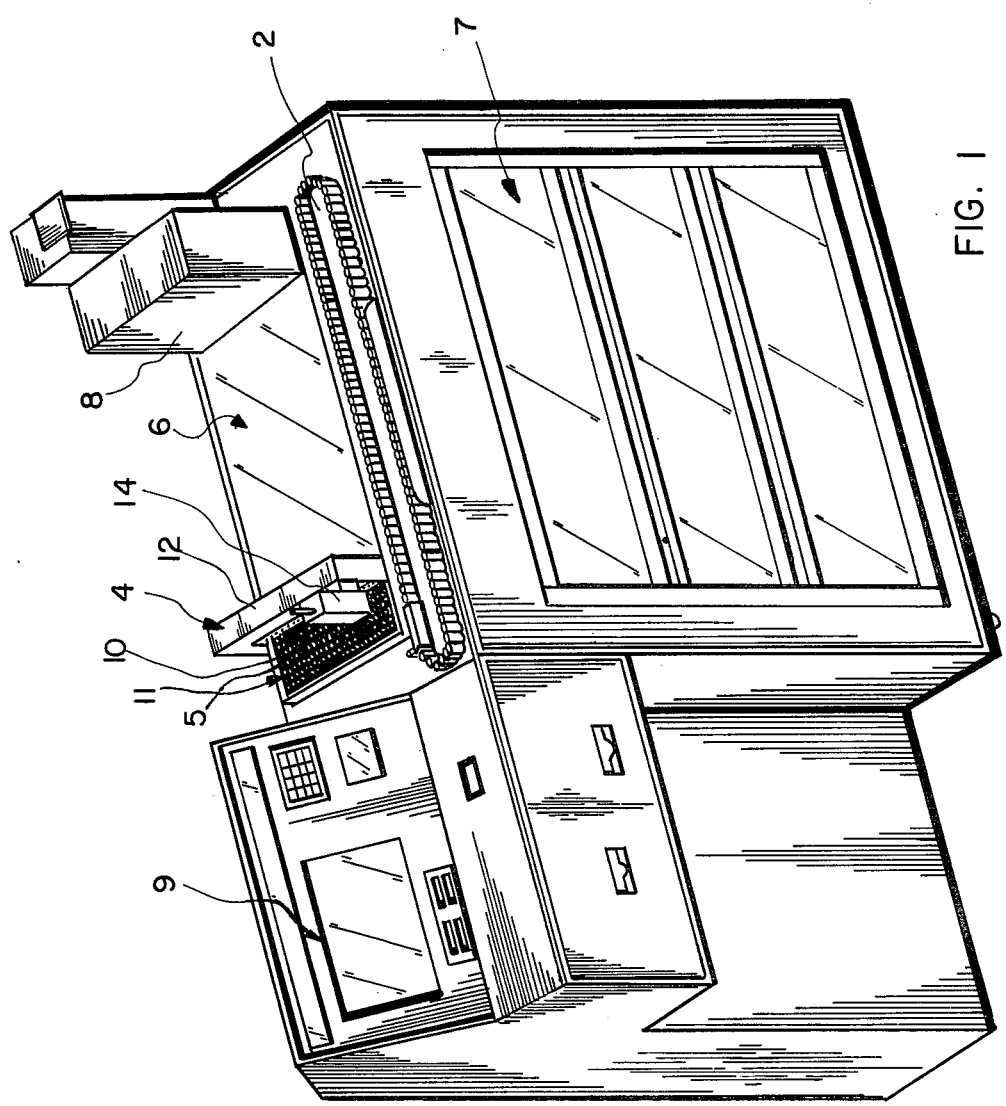
FIG. 1 is an axonometric view of a preferred form of chemical testing apparatus contemplated as the context for the present invention.

Referring now to FIG. 1, it is illustrated an automatic chemical testing apparatus 1 of the type described in the above-cited patents to Moran. Samples in a sample source 2 are successively indexed in timed relationship to an aspiration station 3 for delivery to a sample dispensing means 4 of the present invention. A sample source means 2 may take the form in the above-cited patent to Moran or as illustrated may take the form further described in co-pending patent application, Ser. No. 125,269 filed Sept. 21, 1976. The dispensing means 4 delivers aliquots of each sample to a row 10 containing open-topped reaction containers 11 in a reaction conveyor 5, which indexes each row through successive positions in reaction means including incubation and reagent dispensing stations 6 in which reagents are delivered to selected reaction containers at selected times from a reagent source 7. Adjacent to one row 10 of the conveyor 5, analysis means 8 withdraw reacted contents of reaction containers and provide output signals indicative of concentrations of various substances in a sample. Keyboard and display means 9 are used in place of the control means and recorder of the above-cited Moran patents for display of information and selection of tests to be performed.

Figure 2:
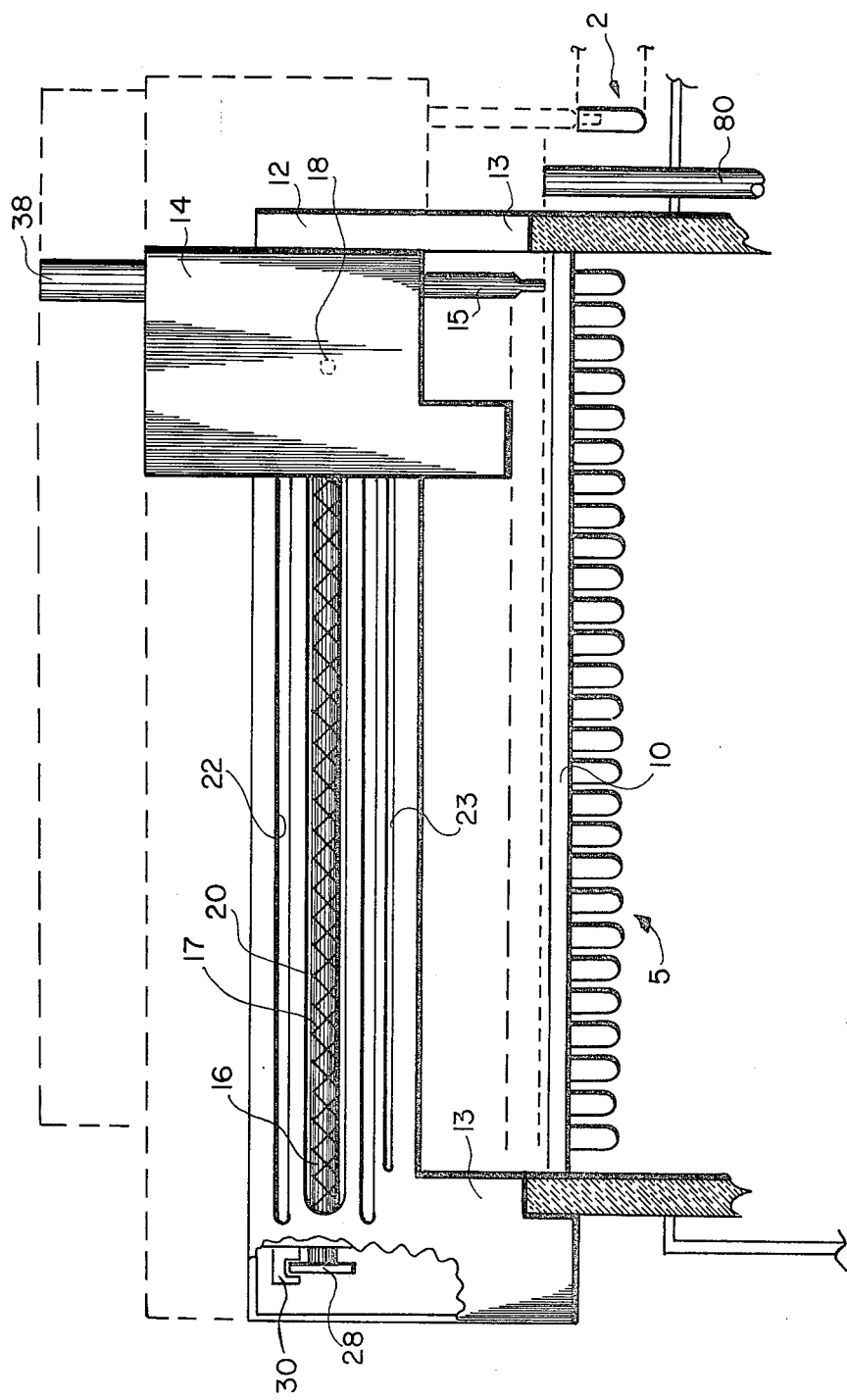
FIG. 2 is an elevation of a sample dispensing means constructed in accordance with the present invention further illustrating the interaction with reaction container carrying means.

Referring now to FIG. 2, there is illustrated a partial side elevation illustrating the sample dispensing means 4 and its spatial relationship to the conveyor means 5. The dispensing means 4 comprises a housing 12 comprising support and drive means and a carriage assembly 14. The carriage assembly 14 carries an aspiration and dispensing needle 15 comprising conduit means. The housing 12 is mounted over the conveyor means 5 by suitable mounting means 13 and contains drive means 16 preferably comprising a double helical cut groove cylinder, hereinafter referred to as the cylinder 16 having a double helical cut groove 17 receiving a pawl 18 mounted on a longitudinally rear side of the carriage assembly 14. This coupling translates rotational motion of the cylinder 16 into transverse linear motion of the carriage assembly 14. A rectangular window 20 in the longitudinally front side of the housing 12 permits coupling of the pawl 18 in the groove 17. Guideways 22 and 23 vertically displaced on either side of the window 20 and extending transversely cooperate with bosses 24 (FIG. 5) for maintaining stability of the carriage assembly 14. A transversely extending rectangular aperture 26 is also provided for permitting electrical connections from the interior of the housing 12 to the carriage assembly 14. A notched disc 28 is provided at one transverse end of the housing 12 and rotated by the cylinder 16 for cooperation with a photosensor means 30 for measuring or monitoring travel of the carriage assembly 14. Control means (FIG. 5) position the carriage assembly 14 such that the aspiration and dispensing needle 15 is positioned at the aspiration station 3. Relative motion is provided between the needle 15 and the sample source and the aspiration station 3 so that the hydraulic circuit (FIG. 3) of the dispensing means 4 can interact therewith. Conventional means may provide for telescoping of the needle 15, or relative motion between the sample source 2 and the needle 15 may be provided by drive means 19, which are further described in co-pending patent application Ser. No. 725,269 filed Sept. 21, 1976. The notched disc 28 is mounted such that a portion of its periphery rotates through a light path defined in the photosensor means 30. In the preferred embodiment, the groove 17 on the cylinder 16 is proportioned with respect to positioning of sample containers in the conveyor means 5 such that rotation of the cylinder by 180 degrees corresponds with linear travel of the carriage means 14 a distance equal to the center to center distance between adjacent reaction containers. Thus by providing notches displaced 180 degrees in the disc 28, the photosensor means 30 provides an output pulse each time the needle 15 travels one reaction container center to center distance. By positioning the fixed angular displacement of the disc 28 with respect to the cylinder 16, phasing, i.e., selection of the position of the needle 15 with respect to each reaction container when a pulse is produced by the photosensor means 30, is selected.

Figure 3:
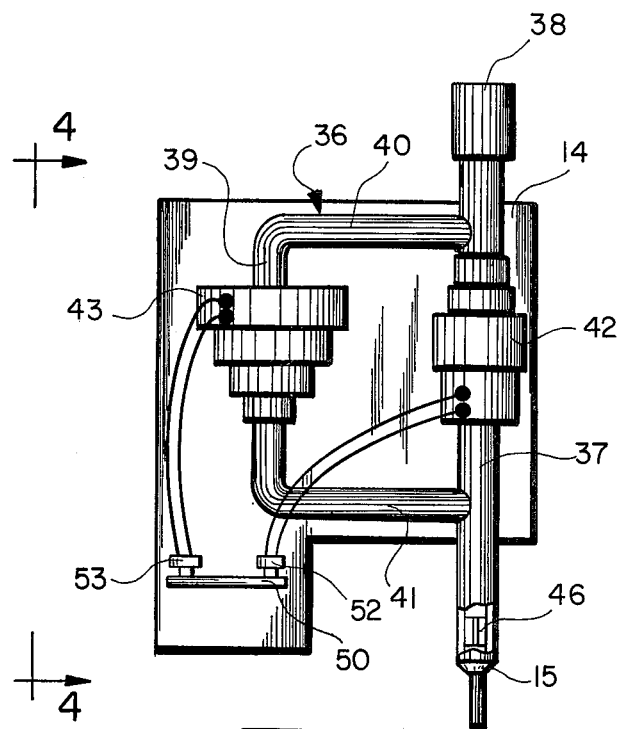
FIG. 3 is a detailed view of the carriage means illustrated in FIG. 2 with the cover removed therefrom to illustrate hydraulic circuitry.

FIG. 3 is an elevation of the carriage assembly 14 with the cover removed therefrom to illustrate the hydraulic circuit therein. A self-priming hydraulic circuit 36 is provided including a vertical leg 37 communicating at one end with the needle 15 and at its upper end with a fluid reservoir 38. The fluid reservoir may house water or preferably mineral oil. The fluid should be immiscible with the sample, which sample will usually be human serum. A second vertical leg 39 is connected in parallel with the vertical leg 38 by upper and lower horizontal legs 40 and 41 on opposite vertical sides of a dispensing pump 42. The vertical leg 39 has connected therein an aspiration pump 43. A spacer 46 is provided for motion inside the needle 15. The spacer consists of a spool having a notched disc at either end of a spindle. The use of the spacer 46 assists in maintaining separation between the fluid in the self-priming circuit 36 and samples to be aspirated, while still permitting a liquid to liquid interface. The spool and disc construction provides for a path for the flow of flushing liquid from the fluid reservoir 38 through the spacer 46 for cleaning the interior of the needle 15. The use of immiscible liquids, the spacer 46, and the provision for flushing are each useful in preventing intersample contamination.

RC circuits 53 and 52 are respectively connected to the aspiration pump 43 and dispensing pump 42 for translating control signals into pulses for operating the solenoid windings thereof. The circuits 52 and 53 are mounted on a printed circuit board 50. The circuit board 50 preferably extends from the assembly 14 into the housing 12 for connection as described with respect to FIG. 4.

The dispensing pump 42 and aspiration pump 43 comprise solenoid pumps with plungers therein containing check valves, and each include conventional means for biasing the plungers to an inactivated position. Upon pulsing the winding of the pump 43, liquid is drawn into the vertical leg 39. Pressure of liquid drawn up in the hydraulic circuit 36 is insufficient to overcome bias on the plunger in the pump 42. Upon pulsing of the winding of the pump 42, liquid is expelled downwardly in the leg 37 of the hydraulic circuit 36. System parameters are selected so that the needle 15 is the path of least resistance for expelling liquid, and the pressure created by the pump 42 does not operate the pump 43.

In the preferred embodiment, the aspiration pump 43 is selected to draw 100 microliters of liquid into the hydraulic circuit 36 each time it is pulsed. The dispensing pump 42 is selected to provide an output of liquid from the hydraulic circuit 36 equal to one aliquot to be dispensed to one of the reaction containers in the conveyor means 5. In the preferred embodiment, the dispensing pump 42 dispenses twenty microliters each time its winding is pulsed.

The solenoid pumps 42 and 43 are preferably of a type providing for fast bursts of small aliquots from the needle 15. An example of such a pump is the solenoid metering pump made by Valcor Engineering Corp., Kenilworth, N.J. Since in the preferred embodiment small aliquots are dispensed, the speed of the drive means 16 can be chosen such that the dispensing pump 42 is pulsed to direct a stream of liquid into each reaction container 11 (FIG. 2) without having to stop the drive means 16. Timing of dispensing is preset, taking into account the diameter of the aperture defined by the open top of each reaction container 11 and the transverse distance between adjacent reaction containers 11.

It should also be noted that as described above, it is highly desirable to maintain a liquid to liquid interface in the needle 15. Since liquid is a substantially incompressable fluid, force applied to sample liquid by liquid in the hydraulic circuit 36 is transmitted directly thereto, with virtually no time delay. Further, since substantially incompressable liquids are utilized, the amount displaced by the pump 42 will equal the amount dispensed from the needle 15. Imprecision due to compression of an intermediate air bubble does not occur. Consequently, dispensing can be performed "on the fly" as the carriage assembly 14 is moving. Thus, mechanisms for starting and stopping the carriage means 14 and proper positioning thereof at each stopped position need not be provided.

Figure 4:
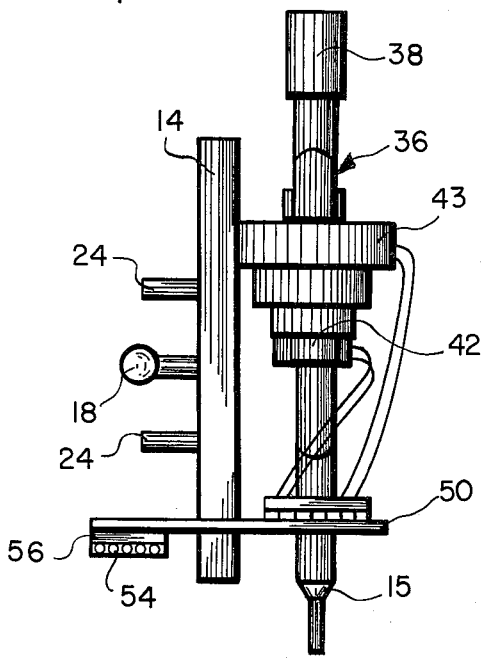
FIG. 4 is an elevational side view of the apparatus illustrated in FIG. 3.

FIG. 4 is an elevational view of the carriage means 14 as it extends in the longitudinal direction illustrating a ribbon cable connector terminal 56 which is mounted to the circuit board 50 and which connects to a flat ribbon cable 54 in the recess 26 (FIG. 2). As the carriage assembly 14 travels in the transverse direction, the ribbon cable 54 doubles back on itself and in the opposite direction straightens out again. In this manner, electrical connections are provided from the moving carriage assembly 14 to fixed wiring in the housing 12 connected to the control circuitry as shown in FIG. 5.

Figure 5:
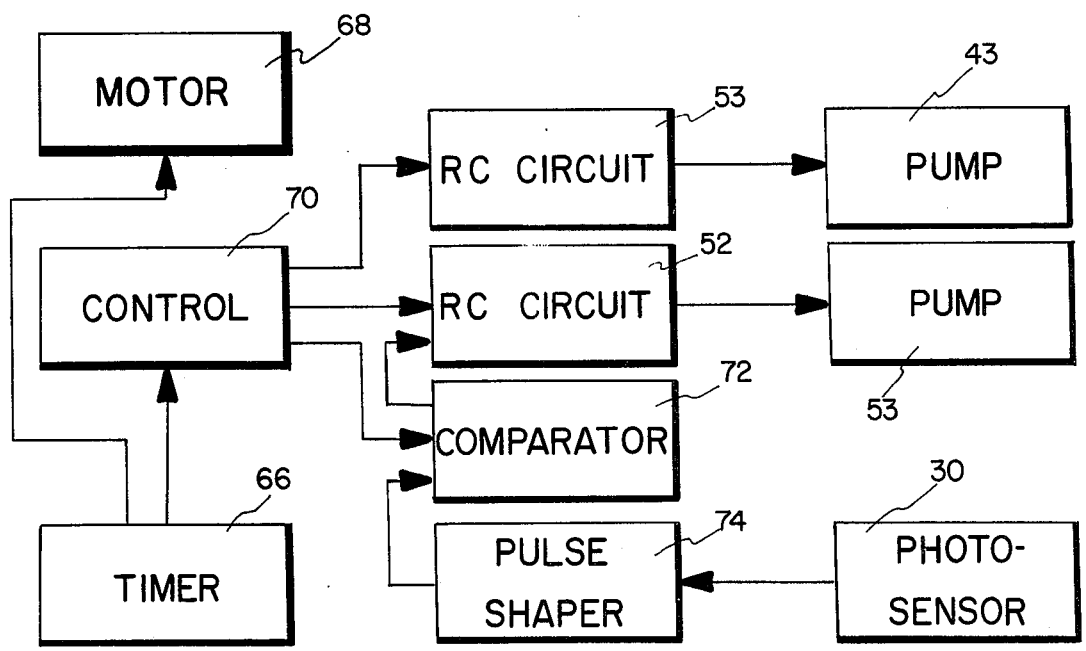
FIG. 5 is a block diagrammatic representation of control circuitry for the apparatus of the present invention.
Figure 6:
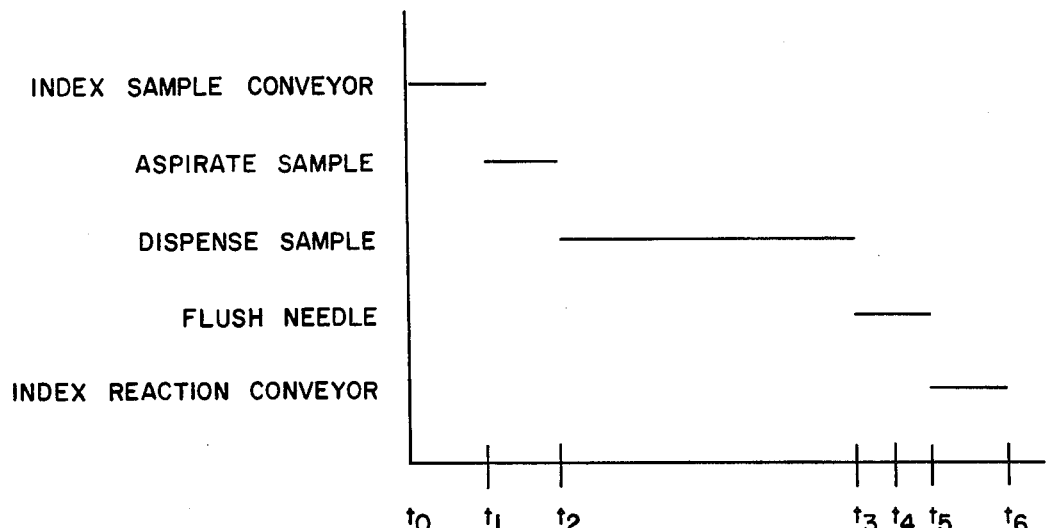
FIG. 6 is a timing chart useful in understanding the operation of the circuitry of FIG. 5 and apparatus of FIGS. 1 through 4.

FIG. 5 is a block diagrammatic illustration of control circuitry for the apparatus as disclosed. A master timer circuit 66 is provided for determining motion of a drive motor 68 which drives the cylinder 16. A control circuit 70, included in the keyboard and display means 9 (FIG. 1) is connected to a comparator circuit 72. The control circuit 70 informs the comparator circuit 72 which tests have been selected to be performed by the automatic chemical testing apparatus 1. In other words, positions are defined of those of the reaction containers along the transverse travel of the needle 15 which must have samples dispensed thereto. Other reaction containers will not have samples dispensed thereto. The photosensor means 30 is connected to a pulse forming circuit 74 providing an input to the comparator 72. The pulse forming circuit 74 informs the comparator circuit 72 which reaction container the needle 15 is in registration with. When there is correspondence between actual position of the needle 15 and position of the needle 15 at which a sample should be dispensed, a pulse is provided to the RC circuit 52 to cause the dispensing pump 42 to dispense an aliquot. The control circuit 70 is also connected to the RC circuits 52 and 53 for commanding aspiration and dispensing as described below.

In a normal operating cycle, illustrated in the chart of FIG. 7, the carriage assembly 14 is moved as described below between the positions outlined in dotted lines in FIG. 2. A now row 10 of the sample conveyor 5 is indexed into position for receiving aliquots between time $t0$ and time $t1$. The control means 70 commands the RC circuit for aspiration between times $t1$ and $t2$. The control circuit 70 informs the pulse producing circuit 74 as to how many tests are programmed to determine the number of times the RC circuit 53 must pulse the pump 43 to aspirate a sufficient sample. For example, if six tests are programmed requiring 120 microliters of sample, the pump 43 will be pulsed twice to aspirate 200 microliters. It is to be remembered that the pump 43 aspirates in units of 100 microliters. From time $t2$ to $t3$ samples are dispensed as described above. In a final mode from times $t4$ to $t5$, the master timer 66 and control 70 operate the pump 43 to flush out all remaining sample and some liquid from the reservoir 38 for cleaning the inside of the needle 15 at a flushing station 80 intermediate the conveyor 5 and the sample source 2. Alternatively, liquid may be flushed into a container in the sample source 2 from which the previously dispensed sample came. The sample source 2 is indexed to provide a new sample at the aspiration station 3 from times $t5$ to $t6$ to complete a cycle.

What is thus provided is an improved system for providing aliquots from a sample source to reaction containers.

What is claimed as new and desired to be secured by Letters Patent of the United States is:

1. In a chemical testing apparatus in which aliquots of a sample are provided to reaction containers in a group supported in reaction means, and wherein sample source means provide samples at an aspiration station, means for aspirating a sample and dispensing aliquots thereof comprising: housing means mounted for defining a path over and in registration with said reaction containers and said aspiration station, carriage means movably supported to said housing means for movement along said path, said path having a fixed spatial relationship to said reaction means, hydraulic circuit means mounted in said carriage means and comprising a self-priming hydraulic circuit, aspiration pump means connected in said hydraulic circuit for withdrawing a measured amount of liquid into said hydraulic circuit each time said aspiration pump means is operated, dispensing pump means connected in said hydraulic circuit for expelling a measured amount of liquid from said hydraulic circuit each time said dispensing pump means is operated, drive means mounted in said housing for driving said carriage means, and control means for operating said aspiration pump means at said aspiraion station, and for providing an output for operating said dispensing pump means at selected points of travel of said carriage means over said reaction containers, and means coupling said control signals to said aspiration and dispensing pump means.

2. The improvement according to claim 1 wherein said aspiration pump means and said dispensing pump means respectively comprised first and second solenoid pumps.

3. The improvement of claim 2 wherein said carriage means further comprises circuit means for translating control signals into pulses for operating said first and second solenoid pump means, and electrical connection means are provided communicating from said carriage means to said housing for connection to a source of control signals.

4. In a chemical analyzer comprising a conveyor having rows of reaction containers which are periodically indexed from a dispensing station through incubation means to a readout station and further including means for adding reagents to said reaction containers and means for providing sample material from a sample source to said reaction containers, the improvement wherein said sample dispensing means comprises housing means supported to said chemical analyzer, carriage means movably mounted to said housing means, said carriage means comprising hydraulic circuit means in said carriage means for aspirating and dispensing to and from a hydraulic circuit therein, conduit means communicating with said hydraulic circuit means at a first end of said conduit means and for aspirating and dispensing at an opposite end of said conduit means, said housing means defining a fixed path for said conduit means in registration with one of said rows of reaction containers and in registration with sample source means, drive means for driving said carriage means in a reciprocating manner from an aspiration station in registration with said sample souce means and over said row, control means for operating said drive means and for operating said aspiration means when said conduit is engaged with a sample source and for operating said dispensing means when said conduit is in registration with predetermined positions above said row, the amount to be dispensed being determined by operation of said dispensing means, and the speed of said drive means being proportioned to the amount of time fluid projected from said conduit is in registration with an opening of one of said reaction containers, whereby said drive means may move said carriage means continuously while said dispensing means is operated.

5. The improvement according to claim 4 wherein said hydraulic circuit means comprises a self-priming closed hydraulic circuit including a first pump mounted therein for aspirating and a second pump mounted therein for dispensing.

6. The improvement according to claim 5 further comprising distance measuring means connected to said drive means for providing periodic outputs indicative of predetermined linear amounts of motion of said carriage means over said row.

7. The improvement according to claim 6 wherein said measuring means comprises a notched disc cooperating with a photosensor.

8. Apparatus according to claim 6 wherein said drive means comprises a rotating double helical cut groove cylinder, and wherein said carriage means is coupled thereto by a pawl mounted in the groove of said cylinder and pivotally fixed to said carriage means, whereby the rotational motion of said cylinder is translated into linear motion of said carriage means.

9. Apparatus according to claim 8 wherein said pumping means each comprise solenoid pumps.

10. Apparatus according to claim 9 wherein said carriage means includes circuit means mounted in said carriage means for translating control signals into pulses for operating each of said solenoid pumps.

11. Apparatus according to claim 10 further comprising electrical connector means mounted to said carriage means and extending into said housing means and further comprising movable cable means in said housing connected to said projection from said carriage means for connection to a source of control signals.

12. Apparatus according to claim 11 wherein said distance measuring means are connected to said circuit means for enabling operation in response to said control means when said conduit is at predetermined positions indicated by said means.

13. Apparatus according to claim 5 wherein said control means further comprises means for moving said carriage means to a flushing position and operating said dispensing pump for flushing said sample from said conduit.

14. Apparatus according to claim 13 wherein said conduit includes spacer means movable in said conduit means for providing an interface between fluid in said self-priming closed hydraulic circuit and liquid aspirated into said conduit means.

15. In a chemical testing apparatus in which aliquots of a sample are provided to reaction containers in a group supported in reaction means, and wherein sample source means provide samples at an aspiration station, means for aspirating a sample and dispensing aliquots thereof comprising: housing means mounted for defining a path over and in registration with said reaction containers and said aspiration station, carriage means movably supported to said housing means for movement along said path, said path having a fixed spatial relationship to said reaction means, hydraulic means and operator means for said hydraulic means mounted in said carriage means for withdrawing a measured amount of liquid into said hydraulic means and for expelling a measured amount of liquid from said hydraulic means drive means mounted in said housing for driving said carriage means, and control means for operating said operator means for aspiration at said aspiration station, and for operating said operator means for dispensing at selected points of travel of said carriage means over said reaction containers, and means coupling said control signals to said operator means.

16. In a chemical analyzer comprising a conveyor having rows of reaction containers which are periodically indexed from a dispensing station through incubation means to a readout station and further including means for adding reagents to said reaction containers and means for providing sample material from a sample source to said reaction containers, the improvement wherein said sample dispensing means comprises housing means supported to said chemical analyzer, carriage means movably mounted to said housing means, said carriage means comprising hydraulic means and operator means for said hydraulic means in said carriage means for aspirating and dispensing, conduit means communicating with said hydraulic means at a first end of said conduit means and for aspirating and dispensing at an opposite end of said conduit means, said housing means defining a fixed path for said conduit means in registration with one of said rows of reaction containers and in registration with sample source means, drive means for driving said carriage means in a reciprocating manner from an aspiration station in registration with said sample source means and over said row, control means for operating said drive means and for operating said operator means for aspiration when said conduit is engaged with a sample source and for operating said operator means for dispensing when said conduit is in registration with predetermined positions above said row, the amount to be dispensed being determined by operation of said operator means, and the speed of said drive means being proportioned to the amount of time fluid projected from said conduit is in registration with an opening of one of said reaction containers, whereby said drive means may move said carriage means continuously while said hydraulic means is operated.

17. The improvement according to claim 16 further comprising distance measuring means connected to said drive means for providing periodic outputs indicative of predetermined linear amounts of motion of said carriage means over said row.

18. The improvement according to claim 17 wherein said measuring means comprises a notched disc cooperating with a photosensor.

19. Apparatus according to claim 17 wherein said drive means comprises a rotating double helical cut groove cylinder, and wherein said carriage means is coupled thereto by a pawl mounted in the groove of said cylinder and pivotally fixed to said carriage means, whereby the rotational motion of said cylinder is translated into linear motion of said carriage means.

20. Apparatus according to claim 19 further comprising electrical connector means mounted to said carriage means and comprising a projection into said housing means and further comprising movable cable means in said housing connected to said projection from said carriage means for connection to a source of control signals.

21. Apparatus according to claim 20 wherein said distance measuring means are connected to said circuit means for enabling operation in response to said control means when said conduit is at predetermined positions indicated by said means.

22. Apparatus according to claim 16 wherein said control means further comprises means for moving said carriage means to a flushing position and operating said hydraulic means for flushing said sample from said conduit.

* * * * *